United States Patent [19]

Tomita

[11] Patent Number: 5,095,912
[45] Date of Patent: Mar. 17, 1992

[54] ARTERIAL DISTENSIBILITY MEASURING APPARATUS

[76] Inventor: Mitsuei Tomita, 7-32, Tachibanadai 1-Chome, Midori-Ku, Yokohama-Shi, Kanagawa 227, Japan

[21] Appl. No.: 521,156

[22] Filed: May 9, 1990

[30] Foreign Application Priority Data

May 19, 1989 [JP] Japan .................................. 1-126070

[51] Int. Cl.$^5$ ............................................ A61B 5/02
[52] U.S. Cl. .................................. 128/672; 128/677; 128/680
[58] Field of Search ............... 128/672, 677, 680, 681, 128/687, 774, 778

[56] References Cited

PUBLICATIONS

Medical and Biological Engineering and Computing, vol. 21, No. 4, Jul. 1983, Stevenage GB, pp. 424–429; Chai et al.
"Noninvasive Determination of Arterial Compliance" Clinical Science, vol. 56, No. 5, 1979, GB pp. 413–417; Gribbin et al.

"Arterial Distensibility in Normal and Hypertensive Man."
Medical and Biological Engineering and Computing, vol. 23, No. 1, Jan. 1985, Stevenage GB, pp. 43–47; Shimazu et al.
"Noninvasive Measurement of Beat-to-Beat Vascular Viscoelastic Properties in Human Fingers and Forearms".

*Primary Examiner*—Kyle L. Howell
*Assistant Examiner*—Scott R. Akers
*Attorney, Agent, or Firm*—Ladas & Parry

[57] ABSTRACT

An arterial distensibility can be measured by putting a cuff with a blood flow shutting bag on an upper arm. The arterial distensibility E can be measured by measuring a shut blood flow critical pressure Pc, a diastolic pressure Pf at the upper arm and a crest value h of a pulse wave transmitted to the upper arm by the expression $E = h/(Pc - Pf)$. The cuff has a forward bag, a central bag and a rear bag. The forward bag functions as a blood flow shutting bag. A pressure change in the forward bag is detected by a forward sensor, and a pressure change in the rear bag is detected by a rear sensor. Based on these detected values, the shut blood flow critical pressure Pc, diastolic pressure Pf and the crest h are given.

4 Claims, 9 Drawing Sheets

ARTERIAL DISTENSIBILITY MEASURING APPARATUS

BACKGROUND OF THE INVENTION

This invention relates to an arterial distensibility measuring apparatus, specifically to an arterial distensibility measuring apparatus which can directly measure arterial distensibility by a simple method.

It is very effective to diagnose heart diseases to know arterial distensibility as well as blood pressure and pulse wave analysis. Healthy people's arteries have soft walls with high distensibility, but arteriosclerosis' arteries have hard walls with low distensibility. Conventionally, the arterial distensibility has been indirectly measured by measuring the transmitting speed of a pulse wave. That is, the characteristic that arteriosclerosis increase the transmitting speed of the pulse wave has been used in measuring the transmitting speed of a pulse wave between the carotid artery and the femoral artery of a femoral by pulse wave sensors attached respectively thereto, and based on the measured transmitting speed, the arterial distensibility has been judged.

But, this conventional measurement of the arterial distensibility has a problem that pulse wave sensors have to be attached to a part near the heart and to a femoral, which makes the measuring operation bothering. Another problem is that this measurement is an indirect determination of the arterial distensibility by the transmitting speed of a pulse wave, and accordingly the measurement is not exact.

SUMMARY OF THE INVENTION

An object of this invention is to provide an arterial distensibility measuring apparatus which can directly measure the arterial distensibility by a simple method.

A first invention of this application relates to an arterial distensibility measuring apparatus comprising:

a blood flow shutting bag for shutting blood flow at a part to be measured of arteries;

critical pressure measuring means for measuring a shut blood flow critical pressure at which shut blood flow state of the part to be measured is released;

diastolic measuring means for measuring a diastolic pressure at the part to be measured;

pressure change detecting means for detecting a pressure change of the blood flow shutting bag based on a pulse wave at the part to be measured;

arterial distensibility measuring means for dividing a crest value of the detected pressure change by a difference between the shut blood flow critical pressure and the diastolic pressure to determine an arterial distensibility.

A second invention of this application relates to an arterial distensibility measuring apparatus comprising:

a cuff including a forward bag for shutting blood flow at a part to be measured of the arteries, a central bag having a larger volumn than the forward bag and disposed downstream thereof, and a rear bag having a smaller volume than the central bag and disposed downstream of the central bag, and the central and the rear bags being internally communicated with each other;

a forward sensor for detecting a pressure change generated in the forward bag as a forward pulse wave;

a rear sensor for detecting a pressure change generated in the rear bag as a rear pulse wave with a set delay time from a detection time of the forward pulse wave;

agreement judging means for superposing the forward pulse wave on the rear pulse wave with the delay time to judge whether or not lower waveforms of the forward and the rear pulse waves agree with each other with a set precision;

critical pressure detecting means for decreasing inner pressure of the respective bags gradually from a sufficiently high value and recording as a shut blood flow critical pressure a value of inner pressure at a time when the rear sensor generates a first proper output;

diastolic pressure detecting means for decreasing inner pressure of the respective bags gradually from the shut blood flow critical pressure and recording as a diastolic pressure a value of inner pressure at a time when the agreement judging means judges an agreement; and arterial distensibility measuring means for dividing a crest value of the detected forward pulse at a set time by a difference between the recorded shut blood flow critical pressure and the recorded arterial distensibility.

A third invention of this application relates to the above described arterial distensibility measuring apparatus, in which the agreement judging means superposes the forward pulse wave and the rear pulse wave so that the rising part of the former and that of the latter agree with each other and judges whether or not the waveforms of both pulse waves below the dicrotic notch pressure agree with each other with set precision.

A fourth invention of this application relates to the above described arterial distensibility measuring apparatus, in which the shut blood flow critical pressure detecting means and the diastolic pressure detecting means are operative to stop temporarily decreasing the inner pressure in the respective bags when the inner pressure has reached intended pressures of both means to confirm that the inner pressure has reached their intended pressures.

The inventions of this application give a shut blood flow critical pressure and a diastolic pressure, at a part to be measured. A difference between the two pressures corresponds to a pressure difference $\Delta P$ generated in the arteries corresponding to the presence of a pulse wave. On the other hand, pressure changes of the blood flow shutting bags are detected based on a pulse wave in the part to be measured, and this pressure change corresponds to an expansion ratio e of the arteries. That is, when the pressure difference $\Delta P$ is applied to the arterial wall, the arteries expand by an expansion ratio e. Then a value given by $E = e/\Delta P$ is an index of distensibility of the arteries.

In the inventions of this application, a cuff having three bags is used to give the shut blood flow critical pressure and the diastolic pressure. Pressure in the respective bags is decreased gradually from a sufficiently high state, and a pressure at the time when the shut blood flow by the most upstream forward bag is released is given as a shut blood flow critical pressure. A pressure at the time when the lower parts of pulse waves detected by the forward and the rear bags agree with each other is given as a diastolic pressure. This method for giving the diastolic pressure is a novel one that has never been proposed by any one other than the inventor of this application.

BRIEF DESCRIPTION OF THE DRAWINGS

FIGS. 14 and 15 are graphs explaining the method of recognizing an arrival at the point F in FIG. 13a.

DESCRIPTION OF THE PREFERRED EMBODIMENT

Figure 1:
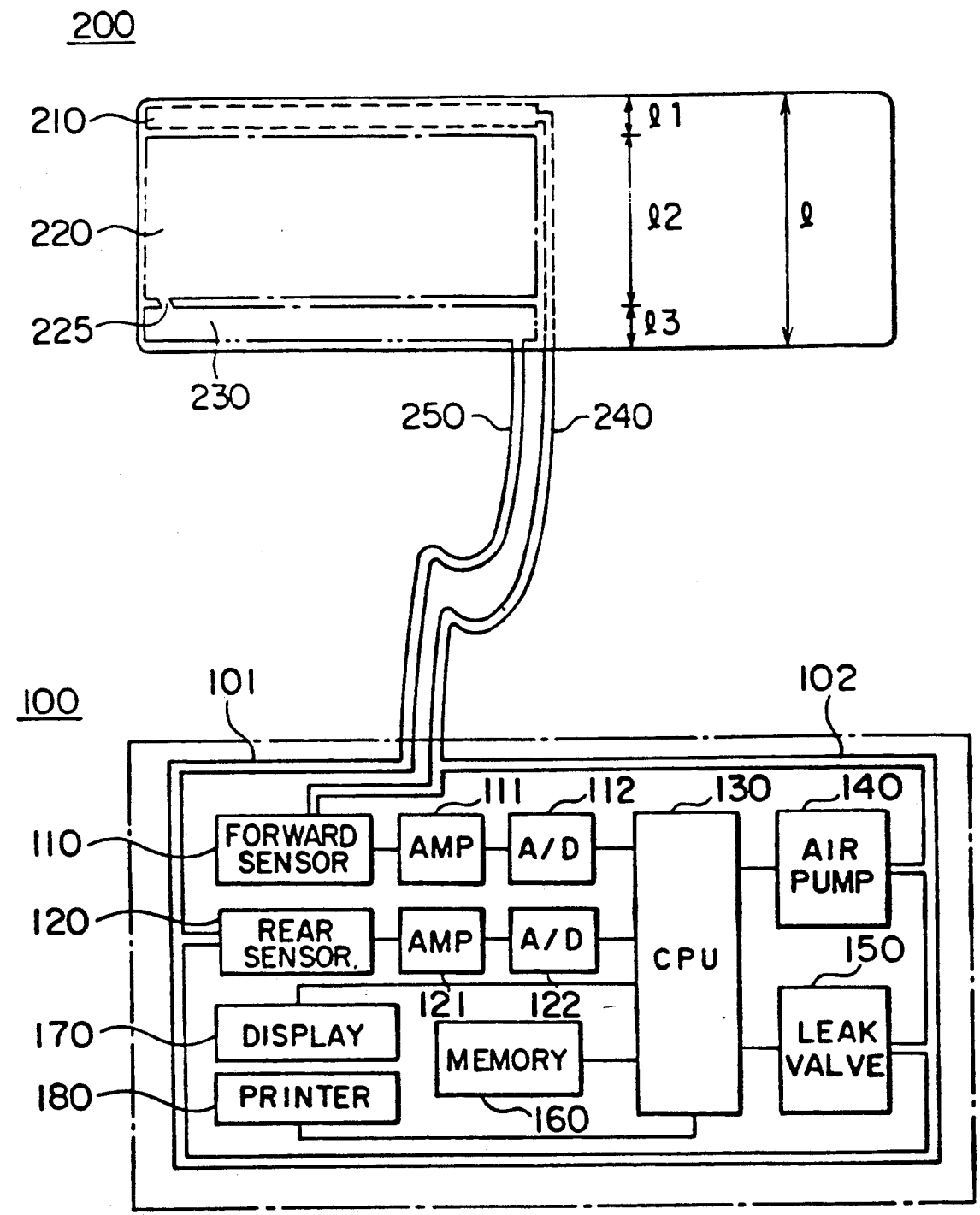
FIG. 1 is a block diagram of an arterial distensibility measuring apparatus according to one embodiment of this invention.
Figure 2:
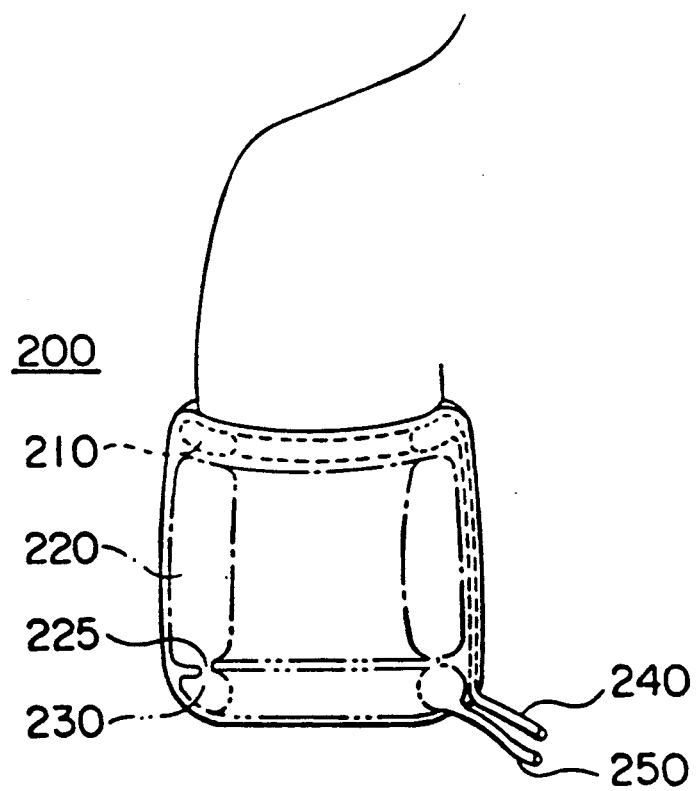
FIG. 2 is a view of the cuff in the device of FIG. 1 put on the upper arm.
Figure 3:
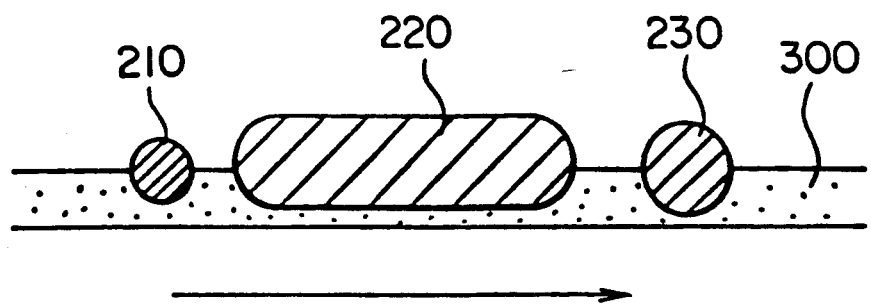
FIG. 3 is a sectional view of FIG. 2 where the artery is pressed by the cuff.

This invention will be explained below by means of an embodiment thereof shown in the drawings. FIG. 1 is a block diagram showing the basic structure of the device involved in the embodiment. This device largely comprises a device body 100 (enclosed by a one dot chain line), and a cuff 200. The cuff 200 has three separate bags, a forward bag 210 (indicated by a broken line, a central bag 220 (indicated by a one dot chain line) and a rear bag 230 (indicated by a two dot chain line). The central bag 220 and the rear bag 230 are communicated with each other by a communication passage 225. In this embodiment, the total width of the cuff l=14 cm, and the respective bag widths are around l1=1.5 cm, l2=10 cm and l3=2.5 cm. As will be described later, the central bag 220 functions as a low pass filter, and to this end it has a larger width compared with the forward and the rear bags 210, 230. The forward bag 210 is connected to a conduit 240 extended outside for feeding air thereinto. The rear bag 230 is connected to a conduit 250 extended outside for feeding air thereinto. This cuff is put on an upper arm in the arrangement shown in FIG. 2. With the cuff put on an upper arm as shown in FIG. 2, when air is fed into the respective bags to build a pressure therein, the respective bags press the artery 300 there as shown in section of FIG. 3. When the pressure becomes sufficiently high, the blood flow through the arteries is completely shut there. In this condition, a pulse wave, which has been propagated from the left, impinges on the forward bag 210 and blocked thereby. When the pressure in the forward bag 210 comes to be a little decreased, the high frequency component of this pulse wave passes the forward bag 210 to impinge on the central bag 220. The larger volume of the central bag 220 hinders the pulse wave from arriving at the rear bag 230. But since the rear bag 230 is in communication with the central bag 220 through the communication passage 225, upon the high frequency component of the pulse wave impinging on the central bag 220, a little pressure change takes place in the rear bag 230 through the communication passage 225. When, the pressure of the central bag 220 is further decreased to pass the pulse wave, the pulse wave passes the central bag 220 and impinges on the rear bag 230. At this time, a conspicuous pressure change due to this impingement takes place in the rear bag 230.

On the other hand, the device 100 has the following structure. A tube 102 connected to the conduit 240 is connected to a forward sensor 110, and a tube 101 connected to the conduit 250 is connected to a rear sensor 120. The forward sensor measures the pressure of the forward bag 210, and the rear sensor measures the pressure of the rear bag 230. Both sensors are so designed that they can sufficiently detect the frequency band of the pulse waves. The analog signal detected by the forward sensor 110 is amplified by an amplifier 111, is converted into a digital signal, and is supplied to a CPU 130. Similarly the analog signal detected by the rear sensor 120 is amplified by an amplifier 121, is converted into a digital signal by an A/D converter 122 and is supplied to the CPU 130. The tube 102 connected to the conduit 240 is connected to an air pump 140 and a leak valve 150. The air pump 140 and the leak valve 150 are controlled by the CPU 130. The tube 101 and the tube 102 are interconnected to each other, and the central bag 220 and the rear bag 230 are interconnected to each other by the communication passage 225. Accordingly the three bags can have the same pressure. The volume of the central bag 220, however, is larger, and due to its larger volume, a pressure change of a high frequency takes place only in the forward bag 210, and it is only when a pulse wave which has been filtered by the central bag 220 impinges directly on the rear bag 230 that a pressure change takes place in the rear bag 230. Accordingly it is preferable to locate the forward and the rear sensor 110, 120 near the conduits 240, 250 respectively. The CPU 130 is connected to a memory 160 for storing data, a display 170 for displaying the data, and a printer 180 for outputting the data.

Figure 4:
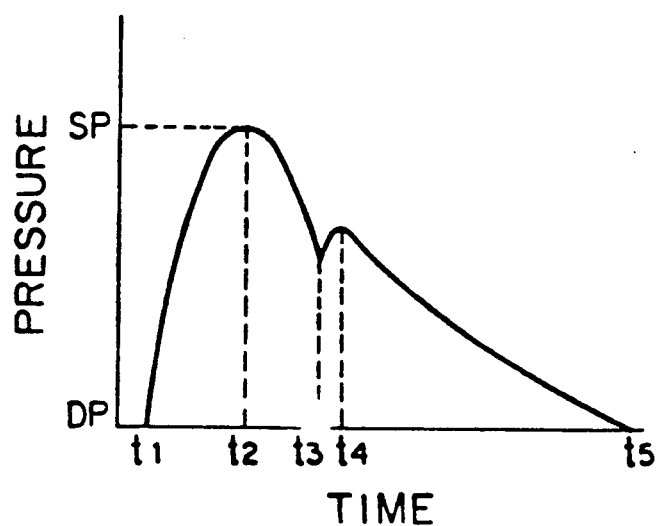
FIG. 4 is a view of the waveform of the usual aortic wave.
Figure 5:
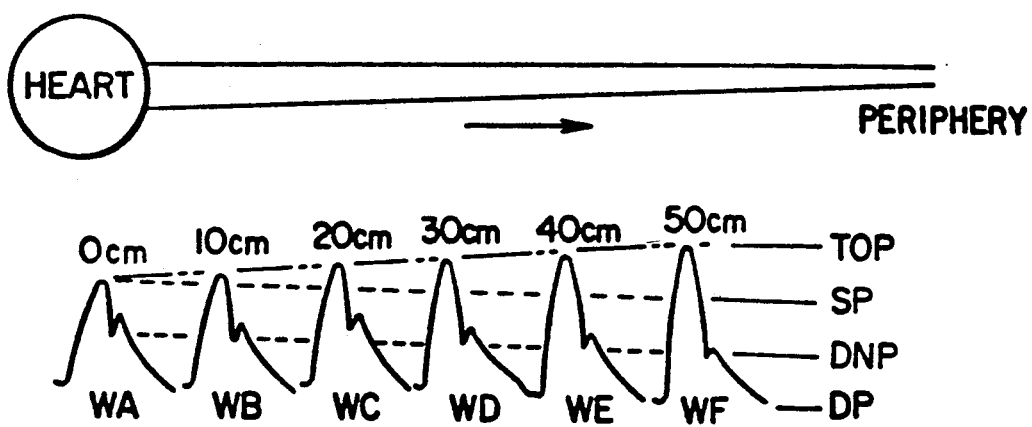
FIG. 5 is a view of changes of a pulse wave from the heart to the periphery.

The pulse waves which arrive at the cuff 200 are supplied by aortic waves. Here it is explained what the aortic wave is. The basic waveform of the aortic wave is shown in FIG. 4. As shown in FIG. 4, the aortic wave is plotted by taking time along the horizontal axis and taking pressure along the vertical axis. The aortic wave has the waveform representing a blood pressure change near the heart and the motion of the heart as it is. In FIG. 4, the heart dilates until the time t1 and has a diastolic pressure DP. From the time t1 to t2 the heart contracts and its pressure rises up to a systolic pressure SP. Following this contraction, the heart dilates, but the aortic valve closes, a small crest appearing at the time t4. This crest is called dicrotic notch. Then from the time t4 to the time t5, the pressure gradually decreases, and again the heart has the diastolic pressure DP. These pressure changes take place each beat of the heart and are transmitted as a pulse wave throughout the body from the heart through the arteries. But the pulse wave generated by the heart changes the waveform during the propagation to the periphery. FIG. 5 shows the waveform changes. The waveforms WA to WF are obtained by measuring the pulse wave at parts distant from the position directly above the aortic valve respectively by 0 to 50 cm by a blood vessel catheter. The waveform WA corresponds to the aortic wave near the heart shown in FIG. 4. As seen from the showing of FIG. 5, as the pulse wave is propagated farther to the periphery, the high frequency component increases, and a maximum blood pressure TOP is increasing. This is considered to result from the fact that the blood vessels become more slender toward the periphery, and the resistance increases.

In FIG. 5, DNP represents a dicrotic notch pressure. Since the pulse wave changes the waveform as it is propagated farther to the periphery, the waveform (e.g., WF) of the pulse wave received by the cuff 200 at the upper arm is considerably different from that of its aortic wave near the heart.

Figures 6A, 6B, 6C:
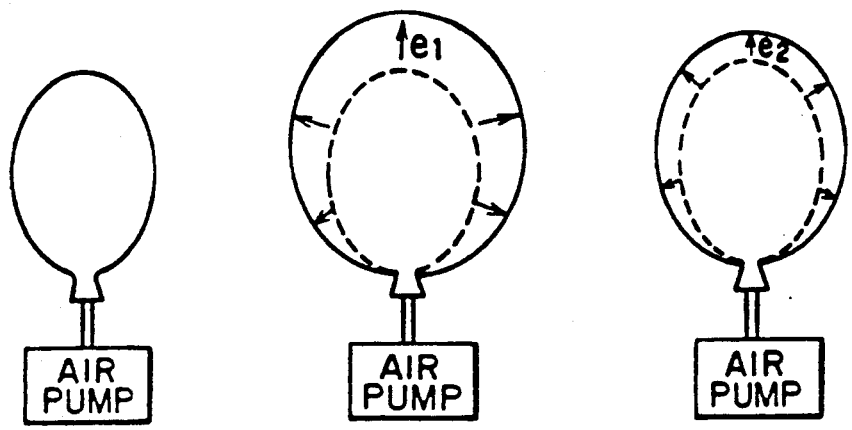
FIGS. 6a, b and c are views of a model for explaining the principle of the arterial distensibility measuring apparatus according to this invention.
Figure 7:
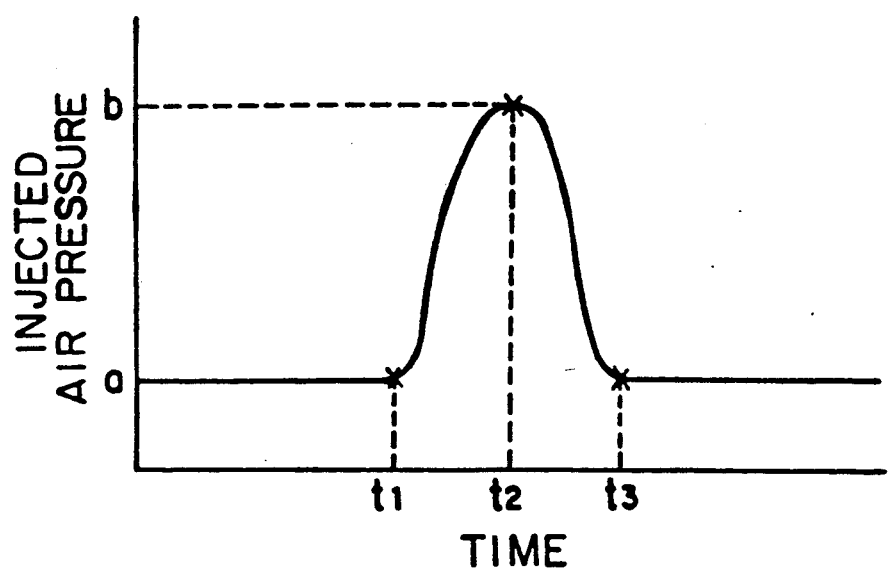
FIG. 7 is a graph of changes of injected air pressure by the air pump in the model of FIG. 6.

Next, the measuring principle of the arterial distensibility by this device will be explained with reference to FIGS. 6a to 6c. Here is assumed a model, as shown in FIG. 6a, in which an air pump is connected to the mouth of an air balloon, and the air pump is so controlled that the air pressure in the balloon has a constant value a. Here, the pressure injected by the air pump is controlled to be as shown in FIG. 7. That is, the air pressure is kept at a until the time t1. FIG. 6a shows this state retained until the time t1. From the time t1 to the time t2 the air pressure is raised from a to b, and the balloon is expanded as shown in FIG. 6b. Subsequently the air pressure is returned to a, and at the time t3 the balloon has been shrunk to the state of FIG. 6a. Here in view of the expansion ratio of the balloon at the maximum expansion time (time t2), it will be seen that the expansion ratio varies depending on the distensibility of the rubber of the balloon. For example, when the air balloon is of soft rubber of high distensibility, the expansion ratio e1 will be considerably high as shown in FIG. 6b, but when the balloon of hard rubber of low distensibility, as shown in FIG. 6c, the expansion ratio e2 will be lower. Thus, the distensibility of the rubber air balloon can be indicated by the expansion ratio e. But, the expansion ratio e is a factor which depends on an injected air pressure. The discussion of the distensibility must take into account pressure differences in the injected air pressures. That is, it is necessary to determine an expansion ratio to an air pressure difference. To this end, the distensibility E is expressed by $$E = e/\Delta P$$

where e is an expansion ratio, and $\Delta P$ is a pressure difference inducing the expansion. In FIGS. 6 and 7, the pressure difference $\Delta P = (b-a)$. Accordingly the distensibility E for the air balloon of FIG. 6b is given by $$E = e1/(b-a),$$

and the distensibility E of the air balloon of FIG. 6c is given by $$E = e2/(b-a).$$

In the above described model, the air balloon is replaced by an artery; the air pump, by the heart; and the waveforms of FIG. 7, by a pulse wave. Then the model can be that of the circulatory organic system. The arteries repeat the dilation and contraction every time a pulse wave as shown in FIG. 7 arrives. Accordingly the distensibility E of the arteries can be given by dividing an expansion ratio e by a pressure difference $\Delta P$. The apparatus according to this invention measures the distensibility of the arteries on this principle.

Figure 8:
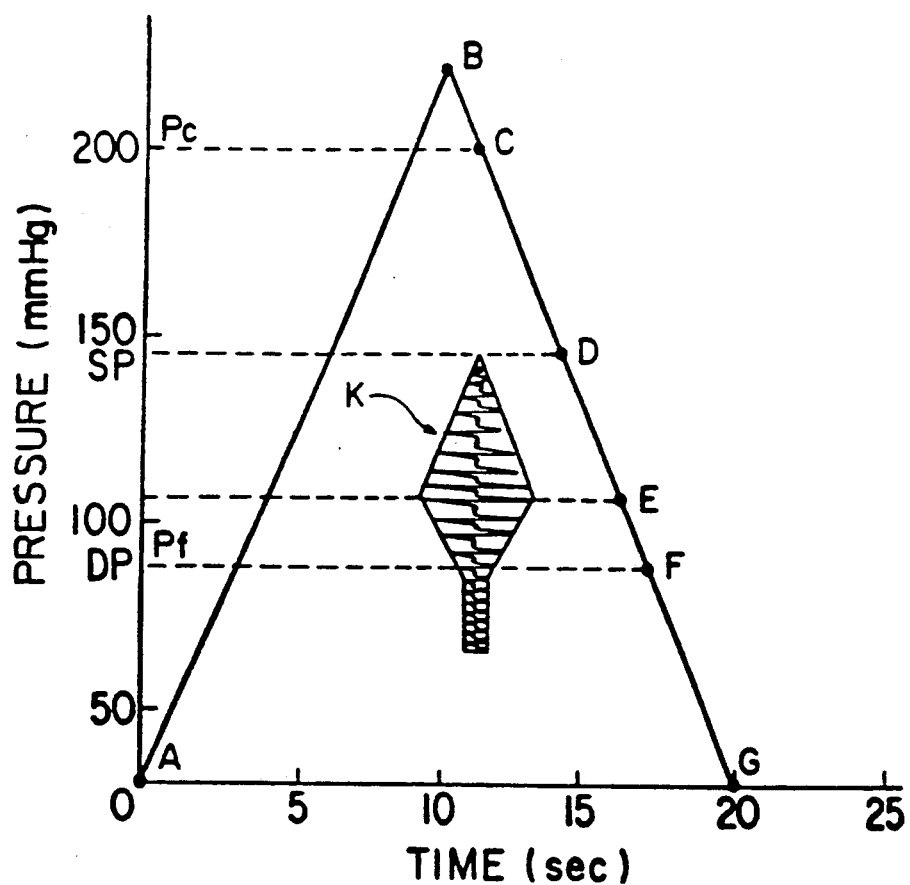
FIG. 8 is a graph of the measuring principle of the device of FIG. 1.
Figure 9:
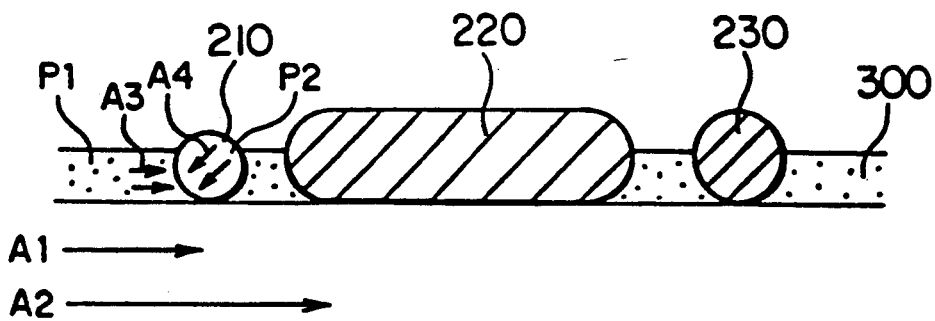
FIGS. 9 and 10 are sectional views explaining the relationships between cuff pressures and passages of pulse waves.
Figure 10A:
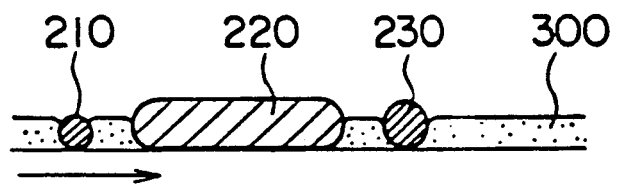
Figure 10B:
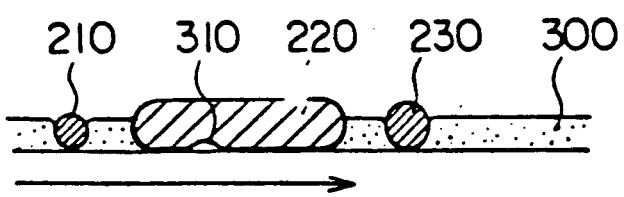
Figure 10C:
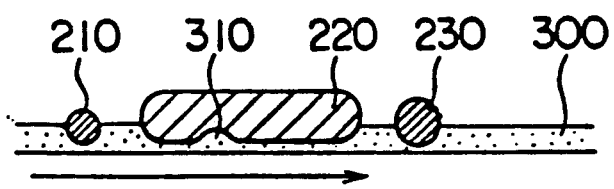
Figure 10D:
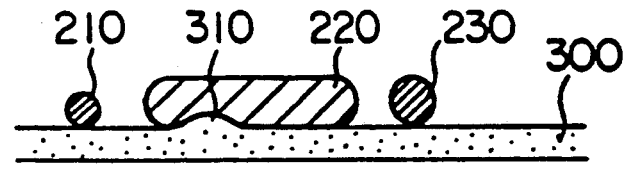
Figure 10E:
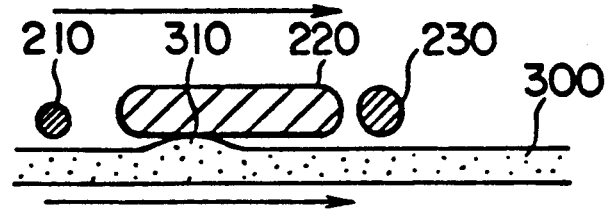

Next, the basic operation of the device of FIG. 1 will be explained. FIG. 8 is a graph for explaining the basic operation. The actual operation a little differs from the basic operation of FIG. 8, but for the convenience of the explanation, the basic operation of FIG. 8 is first explained, and then the explanation of the actual operation will follow. As described above, this device has the air pump 140 and the leak valve 150, and the pressure of the respective bags 210, 220, 230 can be controlled. That is, to increase their pressure, the air pump 140 is actuated to feed air into the bags, and to decrease their pressure, the leak valve 150 is opened to let the air out of the bags. In a measuring operation, the cuff 200 is put on an upper arm of a person for the arterial distensibility to be measured as shown in FIG. 2, and the measurement actuation switch (not shown) is turned on. The graph of FIG. 8 shows changes of the pressure in the bags immediately after the measuring operation is started. That is, after the measuring operation is started, the CPU 130 actuates the air pump 140 to feed air into the bags and gradually increase their pressure (from the point A to the point B). The respective bags 210, 220, 230 press the artery to soon completely shut the blood flow there (the point B). The relationship between the cuff 200 and the artery at this time is shown in section in FIG. 9. The heart is on the left side of the drawing, and the periphery is on the right side, and pulse waves are propagated from the left to the right as viewed in the drawing. But in the presence of the pressure at the point B a pulse wave is blocked by the forward bag 210, and when the pulse wave reaches the position indicated by the arrow A1, it is pushed back. Then the CPU 130 gradually opens the leak valve 150 to decrease the pressure by, e.g., 3 mmHg/sec (from the point B to the point G). Then at a pressure valve Pc, as indicated by the arrow A2 in FIG. 9, the high frequency component of the pulse wave passes the forward bag 210 and impinges on the central bag 220. The point of this impingement is the point C in the graph of FIG. 8. But since the central bag 220 has a larger width and a larger volume than the forward bag 210, the pulse wave cannot still pass the central bag 220. This state is shown also in FIG. 10a. As the pressure is continuously further decreased from the point C, Korotkoff sounds are generated. The Swan type waveforms K in the graph of FIG. 8 indicates the amplitudes of the Korotkoff sounds generated corresponding to the respective values of gradually reduced pressure from the point D. The generation of the Korotkoff sounds at the pressures below the point D is due to that a part 310 of the pulse wave begins to pass the central bag 220 against the resistance thereof as shown in FIG. 10b. It is known that a pressure at the point D corresponds to the systolic pressure SP. As the pressure is continuously farther reduced, the pulse wave passes the central bags with more ease as shown in FIG. 10c. The Korotkoff sound becomes loudest at the point E. Hereafter the Korotkoff sound becomes weaker. When the pressure reaches the point F, the Korotkoff sound becomes very weak, and a substantially constant amplitude continues. It is known that the pressure corresponding to the point F is the diastolic pressure and corresponds to the state of FIG. 10d. As the pressure is continuously farther reduced to the point G, the state of FIG. 10e is obtained. In this state, the bags are apart from the artery 300.

As described above, the basic operation of this device is that in the graph of FIG. 8, the pressure is raised from the point A to the point B and then gradually lowered from the point B to the point G. Next, what outputs the forward sensor 110 and the rear sensor 120 supply at the respective points in the graph will be explained. The pressure change of the forward bag 210 is detected by the forward sensor 110 as described above, and the pressure change of the rear bag 230 is detected by the rear sensor 120. The pressure change of the central bag 220 is transmitted to the rear bag 230 through the conduit 225 to be detected also by the rear sensor 120. But since the central bag 220 has a larger volume, the high frequency component of the pressure change is not detected, and thus the waveform detected by the rear sensor becomes blunt (this waveform is equivalent to the aortic wave).

First, the output of the forward sensor 110 will be explained. As shown in FIG. 9, A whole pulse wave from the heart impinges on the forward bag 210, which is located most upstream. Accordingly, irrespective of the shut blood flow conditions of the respective bags, the forward sensor 110 always detects the whole pulse wave as shown, e.g., in FIG. 11a. From the point B to the point F in FIG. 8, the forward sensor 110 always detects the whole pulse wave of the upper arm. From the point F to the point G, as shown in FIG. 10e, since the forward sensor 210 is apart from the artery 300, the forward bag 210 cannot detect the pulse wave in its perfect form, and the output of the forward sensor 110 gradually diminishes.

Next the output of the rear sensor 120 will be explained. From the point B to the point C in FIG. 8, the whole pulse wave is blocked by the forward bag 210, and the rear sensor 120 cannot detect any of the pulse wave. But at the point C, as indicated by the arrow in FIG. 10a, a part of the pulse wave passes the forward bag 210 to impinge on the central bag 220. The rear sensor 120 supplies any output. But this output is the blunt waveform of a small gain as shown, e.g., in FIG. 11b because the central bag 220 has a larger volume as described above, and the pulse wave has not directly impinged on the rear bag 230. Anyway, the point C in the graph of FIG. 8 is recognized as a point where the rear sensor 120 has supplied any output for the first time. At the point D, as shown in FIG. 10b, a part of the pulse wave passes the central bag 220 to impinge directly on the rear bag 230. The output of the rear sensor 120 becomes sharp and larger. From the point D to the point F in FIG. 8, a larger part of the pulse wave passes the central bag 220, and the output of the rear sensor 120 becomes accordingly larger. At the point F the output of the rear sensor 120 becomes largest (it should be noted that the amplitude of the Korotkoff sound becomes largest at the point E, but the output of the rear sensor 120 becomes largest at the point F). From the point F to the point G, as shown in FIG. 10e, with the rear bag 230 being apart from the artery 300, the output of the rear sensor 120 gradually diminishes.

Figure 12:
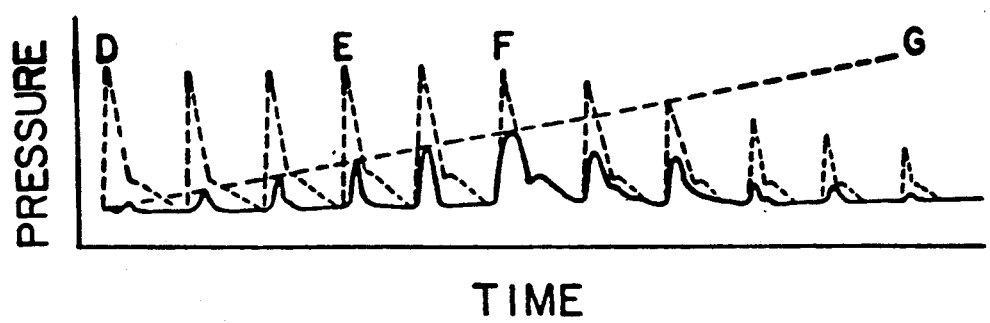
FIG. 12 is a graph comparing the forward pulse wave and the rear wave pulse involved in the device of FIG. 1.

FIG. 12 shows various waveforms detected from the point D to the point G in the graph of FIG. 8. The waveform depicted in the solid line in FIG. 12 is that of the rear pulse wave detected by the rear sensor 120. The waveform depicted in the broken line is that of the forward pulse wave detected by the forward sensor 110 (corresponding to the pulse wave WF in FIG. 5). The reference marks above pulse waves in FIG. 12 represent those detected at the respective points in FIG. 8. The pulse waves without any reference marks given above are those detected between the respective points in FIG. 8. The rear pulse wave depicted in the solid line will be explained. As the pressure is gradually decreased from the point D, the amplitude of the detected rear pulse wave gradually becomes larger. As described above, when the pressure reaches the point F in FIG. 8, the amplitude of the pulse wave becomes maximum and thereafter gradually diminishes. Then the forward pulse wave depicted in the broken line will be explained. The amplitude of the detected forward pulse wave does not change even though the pressure is gradually decreased from the point D. This is because, as described above, the pulse wave can be detected at the forward bag 210 irrespective of the shut blood flow conditions. But past the point F, the amplitude of the pulse wave continuously diminishes. This is because, as described above also, the forward bag 210 becomes apart from the artery 300. Here, in comparison of the pulse wave depicted by the solidline with that depicted by the broken line, it is seen that the high frequency component is cut out. At this point F, the cuff 200 and the artery 300 have the relationship with each other as shown in FIG. 10d. That is, the inner pressure of the cuff 200 and the diastolic pressure DP are equal, so that the pulse wave can fully pass the central bag 220 to give a sufficient impact to the rear bag 230. When the inner pressure of the cuff is higher than the diastolic pressure DP, the ordinary pulse wave cannot pass the central bag 220 as shown in FIGS. 10a to 10c, with the result that a sufficient impact is not given to the rear bag 230. When the inner pressure of the cuff is lower than the diastolic pressure DP, as shown in FIG. 10e, the rear bag 230 leaves the artery 300, with the result that even though the ordinary pulse wave has passed the central bag 220, a sufficient impact is not given to the rear bag 230.

Here, for better understanding, the pressure values detected by the forward sensor 110 and the rear sensor 120 will be briefly explained. The pressure values detected in the forward bag 210 and the rear bag 230 are exactly bag inner pressures of the respective forward bag 210 and the rear bag 230, but each bag inner pressure is divided into pressures of two natures, a reference inner pressure and a change pressure. The reference inner pressure is that shown by the graph of FIG. 8 and is gradually diminished from the point B to the point G. In contrast to this, the change pressure is a pressure change induced every time a pulse wave arrives, and has the waveform of FIG. 12. In short, the pressure value detected by each sensor is a pressure value multiplexing the reference inner pressure and a change pressure. That is, the waveform of FIG. 12 is actually detected in a multiplexed form on the graph of FIG. 8.

Figure 11A:
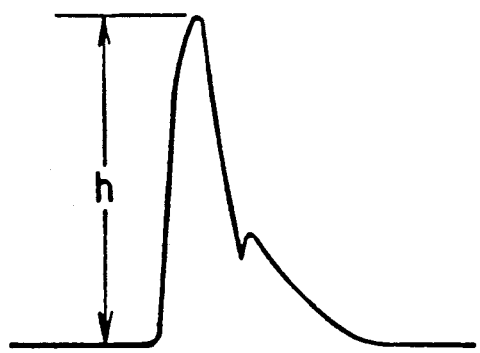
FIGS. 11a and b are views of the output waveform of the sensor of the device of FIG. 1.

Then, the basic priniciple explained above using the air balloon model will be explained below again. According to the model of the air balloon, when an expansion ratio e and a pressure difference $\Delta P$ can be measured, the arterial distensibility E can be given by $E = e/\Delta P$. As a mater of fact, this expression is given by the basic operation of the device shown by the graph of FIG. 8. The expansion ratio e is given as the crest value h of an output waveform of the forward sensor 110. As described above, the output of the forward sensor 110 is as shown in FIG. 11a, and the crest value of this output change is used as a value indicating an expansion ratio e. As described in FIG. 12, the output of the forward sensor 110 is supposed to be intrinsically constant to the point F, and the output at any point between the points B and F may be used. Actually, however, small differences take place among the outputs, and in this embodiment the output at the point F is used. FIG. 10d shows the relationships between the respective bags and the artery 300 at the point F. In the state of FIG. 10d, when a pulse wave passes directly below the forward bag 210, the pressure change of FIG. 11a takes place. It is seen that this pressure change is an amount related with a radial expansion ratio of the vessel wall of the artery 300. If the vessel wall or the artery 300 is soft, the vessel is largely expands to much press the forward bag 210, with the result of a large pressure change.

Then how the pressure change $\Delta P$ is given will be explained. The conclusion is first mentioned. That is, a difference between a pressure value Pc at the point C and that Pf at the point F in the graph of FIG. 8 can be used as the pressure difference $\Delta P$. That is, the air pressures a, b in the model of FIG. 7 correspond to the values Pf, Pc. As described above, it is known that the pressure value Pf at the point F is equal to the diastolic pressure DP, and this diastolic pressure DP is a pressure of the arteries which are not expanded in the absence of a pulse wave. It is easily understood that the pressure value Pf at the point F corresponds to the air pressure a of the air balloon model. Then, in contrast to this, it is considered what pressure the air pressure b corresponds to. The air pressure b is a pressure at the moment when the artery 300 is expanded to a maximum by a pulse wave at the peak. Here the significance of the pressure value Pc at the point C will be considered with reference to FIG. 9. When a pressure P2 of the forward bag 210 is higher than a peak pressure P1 of a pulse wave propagated through the artery 300, the whole pulse wave advances to the position indicated by the arrow A1 and then is pushed back by the forward bag 210. Then the inner pressure P2 is gradually decreased, and the peak pressure P1 of the pulse wave comes to exceed the inner pressure P2 of the forward bag 210. Then the exceeding part of the pulse wave passes the forward bag 210. The pressure value Pc at the point C is the bag inner pressure in this critical state and can be called shut blood flow critical pressure. That is, when the pressure of the forward bag 210 reaches that shut blood flow pressure Pc, the peak pressure of the pulse wave indicated by the arrow A3 is equal to the bag inner pressure indicated by the arrow A4. In short, the shut blood flow pressure Pc is equal to a peak pressure value of the pulse wave propagated through the artery 300.

To summarize what has been described above, the arterial pressure repeats the process starting with the diastolic pressure DP (pressure Pf) followed by a rise up to the shut blood flow critical pressure Pc due to the arrival of a pulse wave and returning to the diastolic pressure DP. The artery is caused by a pressure difference $\Delta P = Pc - Pf$ to expand radially by an expansion ratio corresponding to a crest value h. When the shut blood flow critical pressure Pc, the diastolic pressure Pf and the crest value H of an output of the forward sensor 210 are given, a distensibility E of the arteries can be determined by $$E = h/(Pc - Pf).$$

Next, the specific operation for giving the three values, h, Pc, Pf will be explained below.

The determination of the crest value h of an output of the forward sensor 210 will be first explained. As described above, the output of the forward sensor 210 is supplied to the CPU 130 through the amplifier 111 and the A/D converter 112. If necessary, the waveform of the output can be stored by a memory 160. The CPU 130 easily computes the crest value h, based on the waveform. As described above, in this embodiment the crest value h at the point F in the graph of FIG. 8 is computed.

Figure 11B:
Figure 13A:
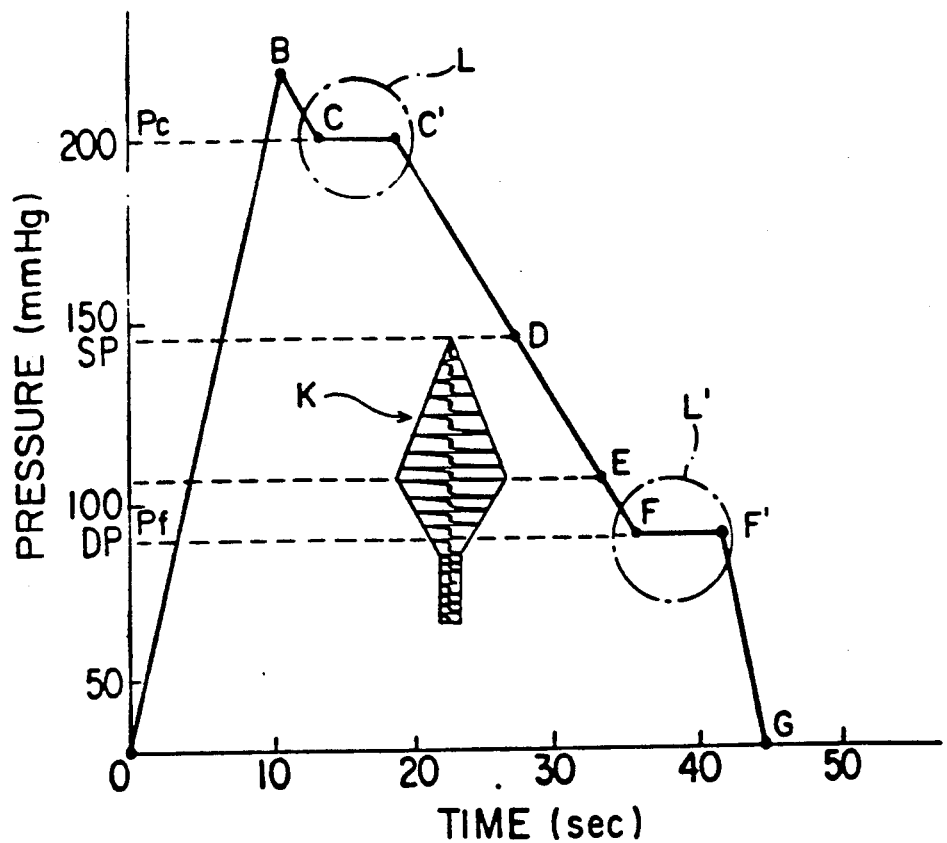
FIGS. 13a, b, and c are graphs explaining the actual measuring operation of the device of FIG. 1.
Figure 13B:
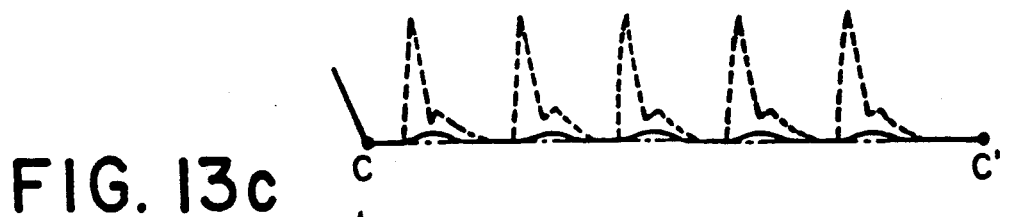

Then, the determination of the shut blood flow critical pressure Pc will be explained. It has been described above that in the basic operation of FIG. 8, the arrival of the pressure at the point C can be recognized by any output as shown in FIG. 11b, supplied by the rear sensor 120 for the first time. In the actual measurement, however, it is possible that the rear sensor 120 supplies an output before the pressure reaches the point C. For example, in the case that a heart happens to supply an arrhythmia, and its pulse wave has a larger amplitude, this pulse wave of the larger amplitude will pass the forward bag 210 even before the pressure reaches the point C and will cause the rear sensor 120 to supply an output. Then actually this embodiment does the operation shown by the graph of FIG. 13a in place of the operation shown by the graph of FIG. 8. In the former operation, at the time when the rear sensor 120 supplies an output for the first time, the decreasing operation of the reference inner pressure is stopped for a while (the point C to the point C') to compare the outputs of the forward and the rear sensors 110, 120. FIG. 13b shows an enlarged view of the part L of FIG. 13a. In FIG. 13b, the one dot chain line (overlapping the solid line) depicts the reference inner pressure; the broken line, the output of the forward sensor 110; and the solid line, the output of the rear sensor 120. Thus, if the pressure has really reached the point C, the output of the rear sensor 120 depicted by the solid line will be the same number of blunt output waveforms as the output waveforms of the forward sensor 110 depicted by the broken line, in synchronization with the latter (the phase is a little shifted). In this example, the synchronization of five waveforms are recognized, and based on this recognition, the arrival at the point C is recognized. Unless the same number of synchronized waveforms appears, it can be judged that the rear sensor 120 happened to supply an output due to an arrhythmia before the pressure reaches the point C, and the reduction of the reference inner pressure can be continued. Thus the shut blood flow critical pressure Pc at the point C can be given accurately.

Next, the determination of the diastolic pressure DP (pressure Pf) will be explained. In this embodiment, as shown by the graph of FIG. 13a, the reference inner pressure is gradually decreased from the point C', and its arrival at the point F is recognized by special method. This recognizing method is based on a novel finding. This method will be detailed based on the basic operation of FIG. 8. First, what forward pulse wave and rear pulse wave are obtained when the reference inner pressure is not the diastolic pressure DP (i.e., at the positions other than the point F in the graph of FIG. 8) will be described. As described above, FIG. 12 shows various pulse waves detected from the point D to the point G in FIG. 8, and the solid line depicts the rear pulse wave detected by the rear sensor 120, the broken line depicting the forward pulse wave detected by the forward sensor 110. The reference marks above pulse waves indicate the pulse waves detected at the respective points in the graph of FIG. 8. The pulse waves without the reference marks indicate the pulse waves detected between the respective points. The rear pulse wave depicted by the solid line will be noted. It has been described above that the pressure is gradually decreased from the point D, the amplitude of a detected pulse wave becomes gradually larger, and when the pressure reaches the point F, the amplitude of the pulse wave becomes maximum and thereafter gradually diminishes, while the forward pulse wave depicted by the broken line does not change its amplitude even though the pressure is gradually decreased from the point D. Here, in comparison of the solid line pulse wave with the broken line pulse wave, it is seen that the high frequency component is cut out. At the point F, the cuff 200 and the artery 300 have the relationship with each other as shown in FIG. 10d. That is, the inner pressure of the cuff 200 and the diastolic pressure DP are equal, so that the ordinary pulse wave can pass the central bag 220 to give a sufficient impact to the rear bag 230. When the inner pressure of the cuff is higher than the diastolic pressure DP, the ordinary pulse wave cannot pass the central bag 220 as shown in FIGS. 10a to 10c, with the result that a sufficient impact is not given to the rear bag 230. When the inner pressure of the cuff is lower than the diastolic pressure DP, as shown in FIG. 10c, the rear bag 230 leaves the artery 300, with the result that even though the ordinary pulse wave has passed the central bag 220, a sufficient impact is not given to the rear bag 230.

Now FIG. 12 will be again discussed. FIG. 12 suggests a very effective method for judging whether or not the reference inner pressure of the cuff has reached the point F, i.e., whether or not the pressure value has been decreased to the diastolic pressure DP. That is, at the point F the forward pulse wave (depicted by the broken line) and the rear pulse wave (depicted by the solid line) exactly agree with each other at the lower portions thereof. Reversely, it can be said that the reference inner pressure of the cuff and the diastolic pressure DP have agreed with each other at the point when their lower portions exactly agree with each other. This is a fact no one other than the inventor of this application has found. It is difficult to make clear the mechanism for this fact theoretically, but the inventor considers that the central bag 220 functioning as a low pass filter cuts at the diastolic pressure DP the high frequency component of an intrinsic waveform of a propagated pulse wave. Accordingly it is necessary that the central bag 220 has a width large enough to function as this low pass filter, and it has been experimentally confirmed that generally a width of 9 cm or more is enough to do this function. The CPU 130 generally diminishes the reference inner pressure from the point C in FIG. 8 while comparing the forward pulse wave of each pulse wave supplied by the forward sensor 110 with the rear pulse wave thereof supplied by the rear sensor 120 and judging that the reference inner pressure has reached the point F when the lower portions of both pulse waves agree with each other.

Figure 14:
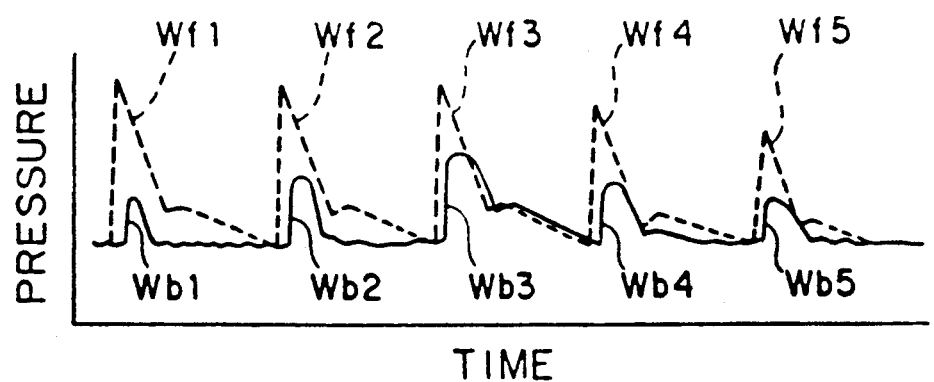
Figure 15:
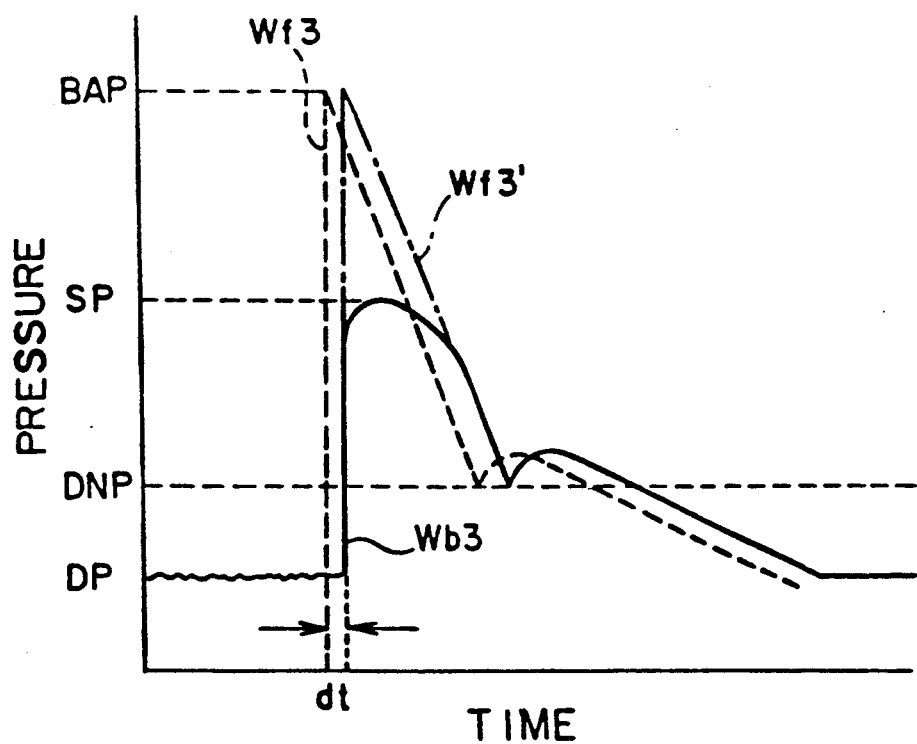

But actually to make the above described judgement, it is necessary to compare both pulse waves, taking into account a delay time of the rear pulse wave. That is, actually the forward pulse wave and the rear pulse wave do not come into the CPU 130 simultaneously. This is because it takes a passing time dt for a pulse wave detected in the forward bag 210 to be detected at the rear bag 230. As shown in FIG. 14, when the forward wave pulses Wf1 to Wf5 and the rear wave pulses Wb1 to Wb5 are respectively compared on the same time axis, actually both are shifted by a delay time. Then the CPU 130 temporarily stores the waveform data of the forward and the rear pulse waves by the memory 160 to delay the forward pulse wave until the rising portions of both pulse waves agree with each other, to multiplex both pulse waves for comparing the lower portions of both pulse waves. FIG. 15 is a view explaining in good detail the operation of comparing the forward pulse wave Wf3 with the rear pulse wave Wb3. The rear pulse wave Wb3 is delayed from the forward pulse wave Wf3 by a delay time dt, but the forward pulse wave Wf3 is shifted to the pulse wave Wf3' to agree the rising portions of the both pulse waves with each other for comparing the lower portions of the pulse waves Wf3' and Wb3. In this embodiment, the lower portion is the waveform below the dicrotic notch pressure DNP. In the example of FIG. 15, the waveforms perfectly agree with each other at the portions below the dicrotic notch pressure DNP. But actually such perfect agreement is impossible, and it is preferable that their agreement with an error smaller than a set error is judged agreement.

Figure 13C:
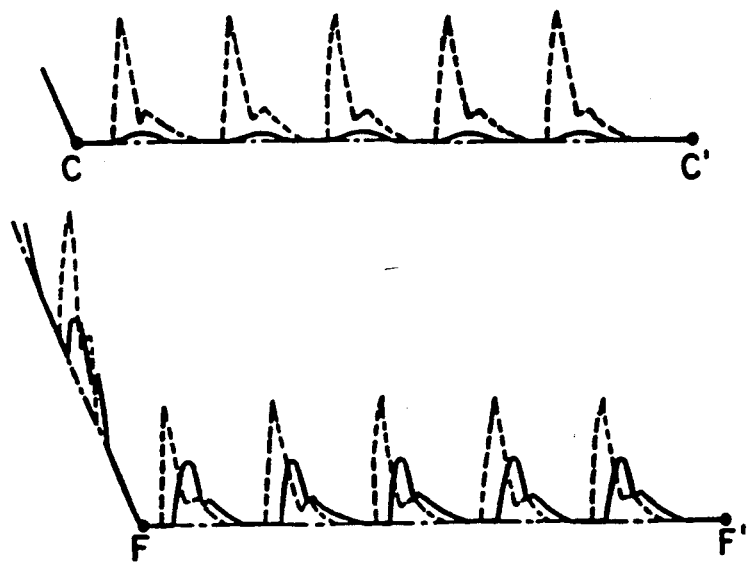

In the device according to this embodiment, when agreement is judged, the CPU 130 stops the operation of the leak valve 150 for a while to retain the reference inner pressure at this level. That is, the reference inner pressure does not pass the point F instantaneously, as shown in FIG. 8, but actually as shown in FIG. 13a, the reference inner pressure is retained at the diastolic pressure DP (pressure Pf) between the points F and F'. The enlarged view of the portion L' of this graph is shown in FIG. 13c. In FIG. 13c, the reference inner pressure is depicted by the one dot chain line (overlapping the solid line), the output of the forward sensor 110 is depicted by the broken line, and the output of the rear sensor 120 is depicted by the solid line. In this embodiment, a pulse wave is measured over five periods between the points F and F'. The agreement can be confirmed with resect to five periods of a pulse wave, which can prevent errors due to accidental agreement. The output waveform of the forward sensor 110 depicted by the broken line is used in determining a crest value h, and the average value of the five periods of a pulse wave can be used as the crest value with resultant higher precision.

In short, in the apparatus according to this invention, as shown in the graph of FIG. 13a, the reference inner pressure of the cuff 200 is changed to thereby measure the arterial distensibility. The shut blood flow critical pressure Pc, the diastolic pressure DP (Pf), and the crest value h due to a pressure change are measured, and the arterial distensibility E can be computed by $$E = h/(Pc - Pf),$$

and the resultant arterial distensibility is displayed on the display device 170 and printed out by the printer 180.

This invention has been explained with reference to one embodiment but is not limited to this embodiment. In summary, this invention gives an arterial distensibility by putting the cuff around an upper arm, measuring the shut blood flow critical pressure and the diastolic pressure generated in the cuff, and dividing a crest value due to a pressure difference generated in the cuff by a pulse wave by a difference between the above described pressures. Accordingly as long as the arterial distensibility can be conducted on this basic principle, any device can be used. In the above described embodiment the lower waveform to be compared is below the dicrotic notch pressure DNP, but the lower waveform may be a different waveform. For example, the part of a waveform corresponding to a lower half of its crest value may be used. Comparing a lower waveform is intended to compare a part other than the high frequency component cut by the central bag. Which part to be compared is optionally selected depending on designs. It is also possible to recognize the arrival at the diastolic pressure by means of the Korotkoff sounds.

According to this invention described above, the arterial distensibility is determined by using a cuff which can shut the blood flow at a part of the arteries to be measured to measure a shut blood flow critical pressure, a diastolic pressure and a crest value of a pressure change due to a pulse wave generated in the cuff, whereby the arterial distensibility is determined. This facilitates directly measuring the arterial distensibility.

What is claimed is:

1. An arterial distensibility measuring apparatus comprising:
    a blood flow shutting bag for shutting blood flow at a part to be measured of arteries;
    critical pressure measuring means for measuring a shut blood flow critical pressure at which shut blood flow state of the part to be measured is released;
    diastolic pressure measuring means for measuring a diastolic pressure at the part to be measured;
    pressure change detecting means for detecting a pressure change of said blood flow shutting bag based on a pulse wave at the part to be measured; and
    arterial distensibility measuring means for dividing a crest value of said detected pressure change by a difference between said shut blood flow critical pressure and said diastolic pressure to determine an arterial distensibility.

2. An arterial distensibility measuring apparatus comprising:
    a cuff including a forward bag for shutting blood flow at a part to be measured of the arteries, a central bag having a larger volume than said forward bag and disposed downstream thereof, and a rear bag having a smaller volume than said central bag and disposed downstream of said central bag, and said central and said rear bags being internally communicated with each other;
    a forward sensor for detecting a pressure change generated in the forward bag as a forward pulse wave;
    a rear sensor for detecting a pressure change generated in the rear bag as a rear pulse wave with a set delay time from a detection time of said forward pulse wave;
    agreement judging means for superposing said forward pulse wave on said rear pulse wave with said delay time to judge whether or not lower waveforms of said forward and said rear pulse waves agree with each other with a required precision;
    critical pressure detecting means for decreasing inner pressure of said respective bags gradually from a sufficiently high value and recording as a shut blood flow critical pressure a value of inner pressure at a time when said rear sensor generates a first proper output;
    diastolic pressure detecting means for decreasing inner pressure of said respective bags gradually from said shut blood flow critical pressure and recording as a diastolic pressure a value of inner pressure at a time when said agreement judging means judges an agreement; and
    arterial distensibility measuring means for dividing a crest value of said forward pulse detected at a set time by a difference between the recorded shut blood flow critical pressure and the recorded diastolic pressure.

3. An arterial distensibility measuring apparatus according to claim 2, wherein the agreement judging means superposes the forward pulse wave and the rear pulse wave so that the rising part of the former and that of the latter agree with each other and judges whether or not the waveforms of both pulse waves below the dicrotic notch pressure agree with each other with a required precision.

4. An arterial distensibility measuring apparatus according to claim 2, wherein the critical pressure detecting means and the diastolic pressure detecting means are operative to stop temporarily decreasing the inner pressure in the respective bags when the inner pressure has reached intended pressures of both means to confirm that the inner pressure has reached their intended pressures.

* * * * *